(12) United States Patent
Karl et al.

(10) Patent No.: US 6,815,217 B2
(45) Date of Patent: *Nov. 9, 2004

(54) USE OF CHECK SURFACES FOR IDENTIFYING DISTURBING SAMPLES IN A DETECTION PROCEDURE

(75) Inventors: Johann Karl, Peissenberg (DE); Helmut Lenz, Tutzing (DE); Friedemann Krause, Penzberg (DE); Peter Finckh, Breitbrunn (DE); Hans Hornauer, Peissenberg (DE); Johann Berger, Graz (AT)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 121 days.

(21) Appl. No.: 09/463,547
(22) PCT Filed: Jul. 20, 1998
(86) PCT No.: PCT/EP98/04533
§ 371 (c)(1), (2), (4) Date: Jan. 21, 2000
(87) PCT Pub. No.: WO99/05525
PCT Pub. Date: Feb. 4, 1999

(65) Prior Publication Data
US 2003/0017616 A1 Jan. 23, 2003

(30) Foreign Application Priority Data
Jul. 22, 1997 (DE) .......................................... 197 31 465

(51) Int. Cl.[7] ............................................. G01N 33/553
(52) U.S. Cl. ...................... 436/518; 436/514; 436/523; 436/524; 436/528; 436/531; 436/513; 435/962; 435/973; 435/974; 435/805; 435/810; 435/7.5; 435/7.9; 435/7.92; 435/7.93; 435/7.94; 435/7.95; 435/5; 422/55
(58) Field of Search ................................ 435/962, 973, 435/974, 805, 810, 7.5, 7.9, 7.92–7.95, 5; 436/514, 518, 523, 524, 528, 531, 825, 807, 220, 513; 422/55

(56) References Cited

U.S. PATENT DOCUMENTS

| | | | |
|---|---|---|---|
| 4,558,013 A | | 12/1985 | Marinkovich et al. ...... 436/513 |
| 5,126,276 A | * | 6/1992 | Fish et al. .................. 436/531 |
| 5,132,085 A | * | 7/1992 | Pelanek ....................... 422/55 |
| 5,160,701 A | | 11/1992 | Brown, III et al. ........... 422/56 |
| 5,356,785 A | | 10/1994 | McMahon et al. ......... 435/7.92 |
| 5,432,099 A | * | 7/1995 | Ekins ......................... 436/518 |
| 5,447,837 A | * | 9/1995 | Urnovitz ........................ 435/5 |
| 5,516,635 A | * | 5/1996 | Ekins et al. ................... 435/6 |
| 5,705,353 A | | 1/1998 | Oh et al. .................... 435/7.92 |
| 5,965,378 A | * | 10/1999 | Schlieper et al. ............ 435/7.9 |

FOREIGN PATENT DOCUMENTS

| | | | |
|---|---|---|---|
| EP | 0 331 068 A1 | 9/1989 | .......... G01N/33/53 |
| WO | WO 96/14338 | 5/1996 | ........... C07K/16/00 |

* cited by examiner

Primary Examiner—Christopher L. Chin
Assistant Examiner—Pensee T. Do
(74) Attorney, Agent, or Firm—Brinks Hofer Gilson & Lione (57) ABSTRACT

A solid phase with at least one test area is described which contains reagents for the detection of at least one analyte in a sample, wherein the solid phase additionally comprises at least one control area for the detection of interfering reactions.

34 Claims, 3 Drawing Sheets

USE OF CHECK SURFACES FOR IDENTIFYING DISTURBING SAMPLES IN A DETECTION PROCEDURE

The invention concerns a solid phase with at least one test area to detect an analyte which additionally comprises at least one control area to detect interferences. Furthermore the invention concerns a method for the detection of one or several analytes using a solid phase according to the invention in which interfering reactions can be detected and corrected if necessary.

When analytes are detected by binding assays interferences in the detection reaction occur with some samples which lead to false test results. This phenomenon is usually referred to as a matrix effect of the sample. The presence of an interference cannot in general be indicated in conventional test formats. It is attempted to prevent matrix effects of the various samples or to reduce them as far as possible by elaborate optimization of the solid phase, test buffers and detection reagent. However, such a reduction of interference in detection methods is complicated and expensive. Moreover one cannot completely rule out the possibility that an adequate reduction of interference does not occur for certain samples despite test optimization since it is unfortunately not possible to completely suppress matrix effects. In addition new interferences which were unknown during the development of the detection method can occur which also lead to false results. Consequently there is a problem that in the known detection methods false test results can be obtained without the user being aware of this. This circumstance is particularly tragic in the case of qualitative tests for the detection of an infectious disease. Thus for example a false positive sample resulting from matrix problems has considerable consequences for a HIV test.

U.S. Pat. No. 4,558,013 describes a test strip which contains a non-defined uncoated negative control region in addition to test regions coated with specific test reagents. The value measured in the test region is corrected by subtracting the unspecific binding in the control region. However, such a procedure can only partially correct for interferences since the unspecific binding of interfering components to the test region usually differs considerably from the binding of interfering components to the uncoated control region.

U.S. Pat. No. 5,356,785 describes a solid phase with several test areas which each contain different amounts of a solid phase receptor for the detection of an analyte. The solid phase additionally contains a reference area which generates a detectable signal of known intensity with the test reagent. Control areas to determine unspecific interactions between the sample and the solid phase are not disclosed.

U.S. Pat. No. 4,916,056 (Brown III et al.) describes a solid phase for the qualitative or quantitative determination of an analyte, in particular of an antigen, antibody or DNA segment in a sample. The solid phase contains, in addition to a test area, a reference area which yields a positive signal in the test and a non-defined negative control area which contains the positive reference area and the test area. A disadvantage of this device is that the surface of the uncoated control region differs too greatly from the test area to achieve an effective correction for interferences.

Hence an object of the invention was to provide devices and methods for the detection of analytes which enable a direct indication of the presence and optionally the type of interferences such that these interferences can be taken into account when evaluating the test results.

This object is achieved according to the invention by a solid phase having at least one defined test area for the detection of an analyte in a sample which is characterized in that the solid phase additionally comprises at least one defined control area for the detection of interferences. In this connection the term "defined test areas" on a solid phase is understood to mean that the test areas comprise defined regions of the solid phase which are preferably spatially separated from other test areas by inert regions. The defined test areas preferably have a diameter of 10 $\mu$m to 1 cm and particularly preferably 10 $\mu$m to 5 mm. Miniaturized test areas with a diameter of 10 $\mu$m to 2 mm are most preferred. Solid phases with several test areas are preferred which are also referred to as array systems. Such array systems are for example described in Ekins and Chu (Clin. Chem. 37 (1995), 1955–1967) and in U.S. Pat. Nos. 5,432,099, 5,516, 635 and 5,126,276. An advantage of array systems is that several analyte and control determinations can be carried out simultaneously on one sample. The use of control areas to detect unspecific binding and/or interfering samples can considerably improve the reliability of the results especially with miniaturized array test systems.

In this connection the detection of interferences and unspecific binding in qualitative tests and in particular in those which have stringent requirements for specificity such as tests for infections (e.g. HIV) are of particular interest. The indication of an interference and correction of the test result enables false-positive results to be considerably reduced thus leading to an enormous improvement of specificity.

The solid phase according to the invention is any conventional support for detection methods, preferably a nonporous support e.g. a support with a plastic, glass, metal or metal oxide surface. Porous supports such as test strips are also suitable. Spatially discrete regions (test areas) are located on this support. Immobilized solid phase receptors are applied to these test areas. The solid phase receptors are immobilized by known methods e.g. by direct adsorptive binding, by covalent coupling or by coupling via high affinity binding pairs e.g. streptavidin/biotin, antigen/ antibody or sugar/lectin. The presence or/and the amount of the analyte in a sample can be determined by specific binding of components from the detection medium e.g. of the analyte to be determined or of an analyte analogue to the solid phase receptor.

The detection of the analyte and the presence of interfering reactions is achieved in the method according to the invention in a known manner by using suitable marker groups e.g. fluorescent marker groups. Alternatively with suitable solid phases it is possible to also detect the interaction of components of the detection medium with the test and control areas by determining the layer thickness of the respective area e.g. by plasmon resonance spectroscopy.

With array systems in which several analytes from a sample are detected simultaneously, it is preferable to use a "universal" marker group which enables a simultaneous detection of several different analytes to different test areas. An example of such universal marker groups are marker groups which carry a receptor that can specifically interact (e.g. by means of a high-affinity binding pair such as antibody/antigen or streptavidin/biotin etc.) with a complementary receptor on a test reagent e.g. a soluble receptor for an analyte to be determined or for an analyte analogue.

Figure 1:
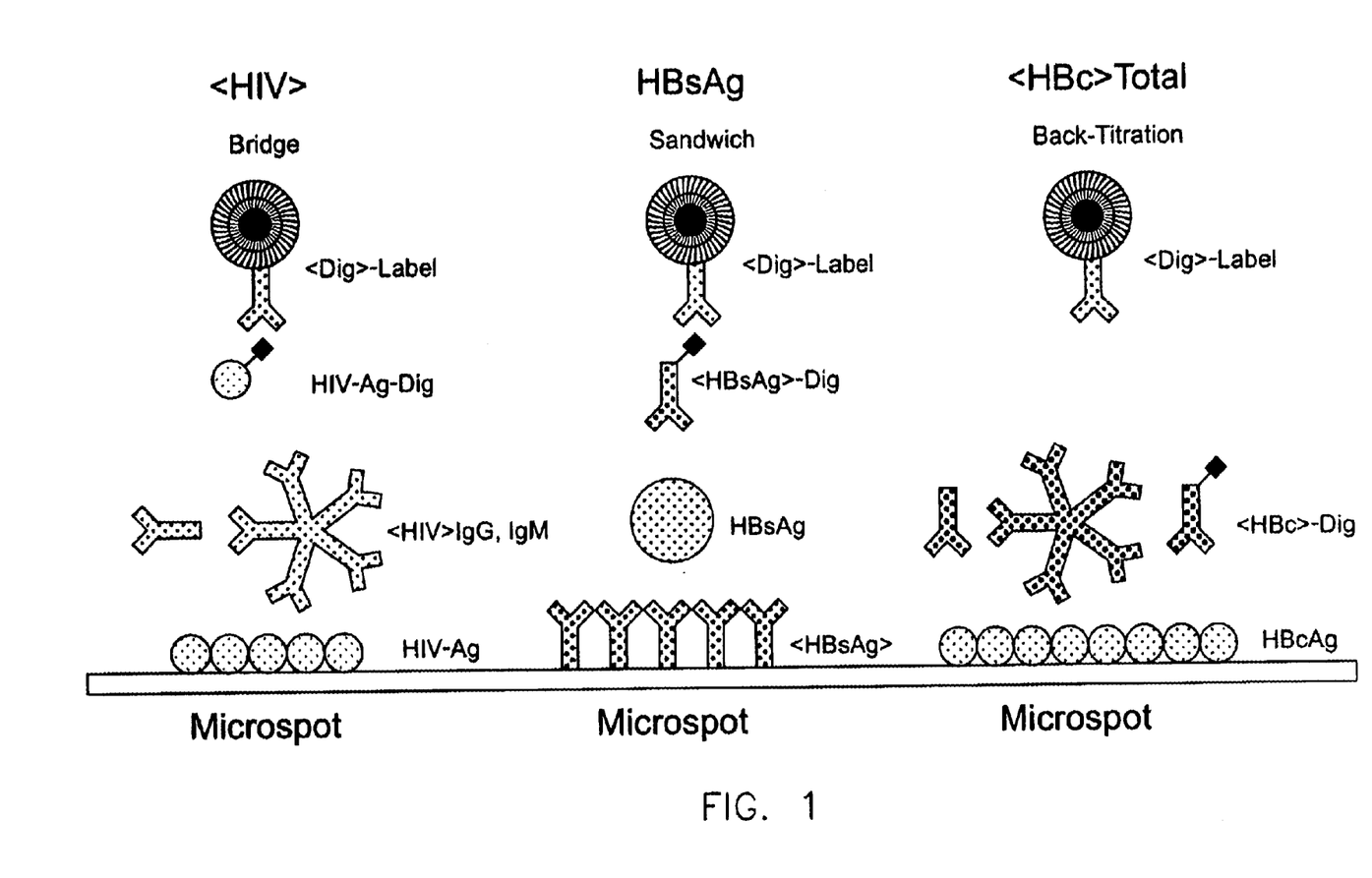
FIG. 1: shows an example of a miniaturized array system (microspot) that uses a universal marker group and allows the simultaneous determination of 3 parameters on a solid phase.

The application of such a universal marker group is exemplified in FIG. 1. In this case a fluorescent latex bead which is coupled with an anti-digoxigenin antibody (<Dig> label) is used for three different test formats on a single solid phase i.e. to determine HIV antibodies, HBs antigen and anti-HBc antibodies. In the case of the anti-HIV antibody determination an immobilized HIV antigen and a digoxigenylated soluble HIV antigen are used which form an immobilized immune complex with the anti-HIV antibodies to be detected. The marker group can bind to the digoxigenin groups present on this immune complex. For the determination of HBs antigen, an immobilized antibody and a digoxigenylated soluble antibody that can interact with the marker group are used in a corresponding manner. A competitive test format is used for the anti-HBc determination in which anti-HBc antibodies present in the sample compete with a digoxigenylated anti-HBc antibody for immobilized HBc antigen. The quantity of marker group bound to the test area is inversely proportional to the anti-HBc concentration in the sample.

Defined test and control areas can additionally contain a detectable and analyte-unspecific marker group which can be detected concurrently with the analyte-specific marker group and does not interfere with it, in order to differentiate them from inert regions of the solid phase. An example of such an analyte-unspecific marker group is a fluorescent marker group which fluoresces at a wavelength which is different from the fluorescent wavelength of an analyte-specific marker group. The analyte-unspecific marker group is preferably immobilized—like the solid phase receptor—via a high affinity binding pair e.g. streptavidin/biotin.

The solid phase according to the invention can be used in any detection methods e.g. in immunoassays, nucleic acid hybridization assays, sugar-lectin assays and similar methods.

The solid phase according to the invention enables a detection of interfering reactions to obtain reliable test results even when the measures known from the prior art for interference reduction are not adequate for certain samples. The control areas not only enable a qualitative detection of interfering reactions but also in many cases enable a quantitative correction for the interference.

The solid phase can comprise several, in particular different control areas for the detection of interfering reactions in order to detect different interferences. In this manner it is possible to specifically detect different types of interference. It is particularly advisable to apply a series of control areas that are suitable for the detection of frequently occurring or/and particularly relevant interfering components for the respective test.

Interference of test procedures can in general be the result of undesired, non-analyte-specific interactions of substances on the test area with components of the detection medium. These substances on the test area may be in particular components of the solid phase, parts of the solid phase receptor and other reagents located on the surface of the solid phase. The interfering components of the detection medium mainly come from the sample (matrix effect) and in some cases lead to unspecific binding of test reagents e.g. of the detection reagent to the solid phase and result in a falsification of the measured signal. Thus interfering interactions between the test area and sample components, test reagents, reaction products or complexes of sample components and test reagents may occur.

The solid phase according to the invention preferably comprises control areas to detect interferences that are due to an undesired binding of components of the detection medium to the specific solid phase receptor for the analyte. Non-analyte interfering components are frequently present in samples such as antibodies or antigens which have a tendency for an increased unspecific binding to the solid phase receptor and in this manner lead to erroneous test results. Hence a control area is particularly advantageous which comprises a non-analyte specific solid phase receptor which, with the exception of the region that can specifically bind to the analyte, is completely identical to the solid phase receptor in the test areas.

If the solid phase receptor is for example an antibody or an antibody fragment, a control area is used which contains an unspecific antibody or an unspecific antibody fragment of the same species, preferably of the same class and particularly preferably of the same subclass as that of the solid phase receptor of the test area. If the solid phase receptor is for example an antigen e.g. a peptide or a polypeptide, a control area is used which contains a mutated "antigen" which differs from an immunologically reactive antigen by modifications e.g. by modifying the smallest possible number of amino acids in the region of immunogenic epitopes. These amino acid modifications can comprise insertions, deletions and preferably substitutions of natural amino acids by other natural amino acids or non-natural amino acid derivatives e.g. D-amino acids. If the solid phase receptor is for example a nucleic acid, a control area is used which contains a "mutated" nucleic acid which differs from the nucleic acid immobilized on the test area by modifications in the nucleotide sequence for example by a base substitution within the sequence responsible for the recognition of a target nucleic acid, preferably in the middle thereof. A mutein of the solid phase receptor is most preferably used which, with the exception of the analyte-specific antigen binding site, is completely identical to the solid phase antibody in the test areas.

It is also preferable that the solid phase receptor applied to the control area has been subjected to identical treatment steps e.g. derivatizations as the solid phase receptor applied to the test area. Thus for example—in the case of a biotinylated solid phase receptor—the number of biotin molecules coupled to the solid phase receptor should be the same in the test area and in the control area. In addition the solid phase receptors in the test area and in the control area should have been subjected to an identical coupling chemistry. In addition identical linkers should also have been used. A solid phase receptor suitable for a control area should not be able to specifically bind to the analyte but preferably comprises all other regions and thus binding sites of the solid phase receptor of the test area. Consequently the unspecific binding of interfering components to the respective solid phase receptor of the test area and control area is essentially identical so that it is possible to quantitatively correct the measured value of the test area on the basis of the measured value of the control area.

The solid phase additionally comprises at least one control area to detect interferences which are caused by the reaction of other immobilized reagents in the test areas with non-analyte components of the sample. As a result interfering components are especially detected that react specifically or/and unspecifically with components of the loading solution used to apply the solid phase receptor. Such a control area can for example contain reagents of the loading solution used in a test system such as buffers, immobilization reagents such as streptavidin, biotinylated substances e.g. biotinylated fluorescent markers, non-analyte specific antibodies etc., blocking reagents or linkers.

Rheumatoid factors often interfere with tests. Hence it is preferable to set up at least one control area on the solid phase to detect rheumatoid factors. Rheumatoid factors are usually IgM molecules but rarely also IgG, IgA and IgE molecules which react with the Fc part of antibodies and interfere with the test if they for example cross-react with the antibody immobilized on the test area or/and a soluble detection antibody, e.g. by cross linking the antibody bound to the solid phase with a labelled detection antibody which results in an unspecifically increased signal. For such a control area an unspecific IgG molecule, preferably the Fcγ part of a human IgG molecule, is applied to the solid phase. Then the rheumatoid factor does not only bind to the test area during the test but also to the control area and thus indicates the interference.

A further interference which occurs relatively frequently is caused by foreign-species-specific antibodies in the sample i.e. antibodies which are directed against antibodies of foreign species e.g. human anti-mouse antibodies (HAMA). Thus the solid phase according to the invention also preferably comprises at least one control area to test for foreign-species-specific antibodies. Foreign-species-specific interfering components e.g. HAMA lead for example in a double antibody sandwich assay to a cross linking of the solid phase antibody with the detection antibody and consequently to an unspecifically increased signal. An unspecific antibody of the same species as the test antibody is preferably used for a suitable control area. A HAMA interfering component which may be present in the sample binds to the antibody applied to the control area which indicates the interfering reaction.

Instead of a solid phase receptor that is identical with the detection reagent in the test area apart from the specific analyte-bindable region, the complex formed during the detection reaction e.g. solid phase antibody-analyte-detection antibody (without label) can also be applied to a control area so that a specific reaction is no longer possible although the unspecific binding sites are almost identical with those of the test area.

Interfering components in the serum are also known which are directed against neo-epitopes of an antibody fragment. Such neo-epitopes are formed for example during the $F(ab')_2$ cleavage of an IgG molecule. In this case it is preferable to provide a control area which contains a fragment of an unspecific antibody which has been produced by the same method (cleavage conditions and cleavage protein) as the antibody fragments of the test area. The interfering components bind to these unspecific antibody fragments and can therefore be detected.

In addition it is also possible using suitable control areas to detect interfering components which may be present in a sample e.g. interfering antibodies that are directed against immobilization reagents on the test areas such as streptavidin. For this purpose streptavidin (SA) is applied to a control area and labelled SA is added to the detection reagent. If anti-SA antibodies are present in the sample, a sandwich complex is formed and the antibody is specifically detected.

The solid phase according to the invention can further contain a control area to detect the total IgE content. Such a control area is particularly recommended for allergy tests. When specific IgEs are determined in allergy diagnostics samples with a high total IgE content often interfere with the specific detection reaction of a certain IgE. The total IgE content can be determined in parallel to the detection method with the aid of a control area on which anti-IgE antibodies have been applied.

Finally control areas can also be provided to detect interferences that are caused by reactions of components of the detection medium with the solid phase support. For this purpose all components of the solid phase support such as the support material (e.g. polystyrene), plasticizer, functional groups etc. can be applied to a control area.

In addition control areas to determine a cut-off value can be used for certain test procedures e.g. in qualitative or semi-quantitative tests for infectious diseases, allergies etc. The "cut-off" value is a threshold value that is set for test procedures in order to differentiate between positive and negative values. Such a "cut-off" value is of particular importance for test procedures which relate to infectious diseases. One possibility is to use a "negative" control area which can contain a loading solution without the test reagent or a mutein of the test reagent. A major advantage is that a sample-specific value for the unspecific binding is determined for each sample and thus an improved specificity of the test is obtained. In this manner a separate negative control can be omitted.

Figure 2:
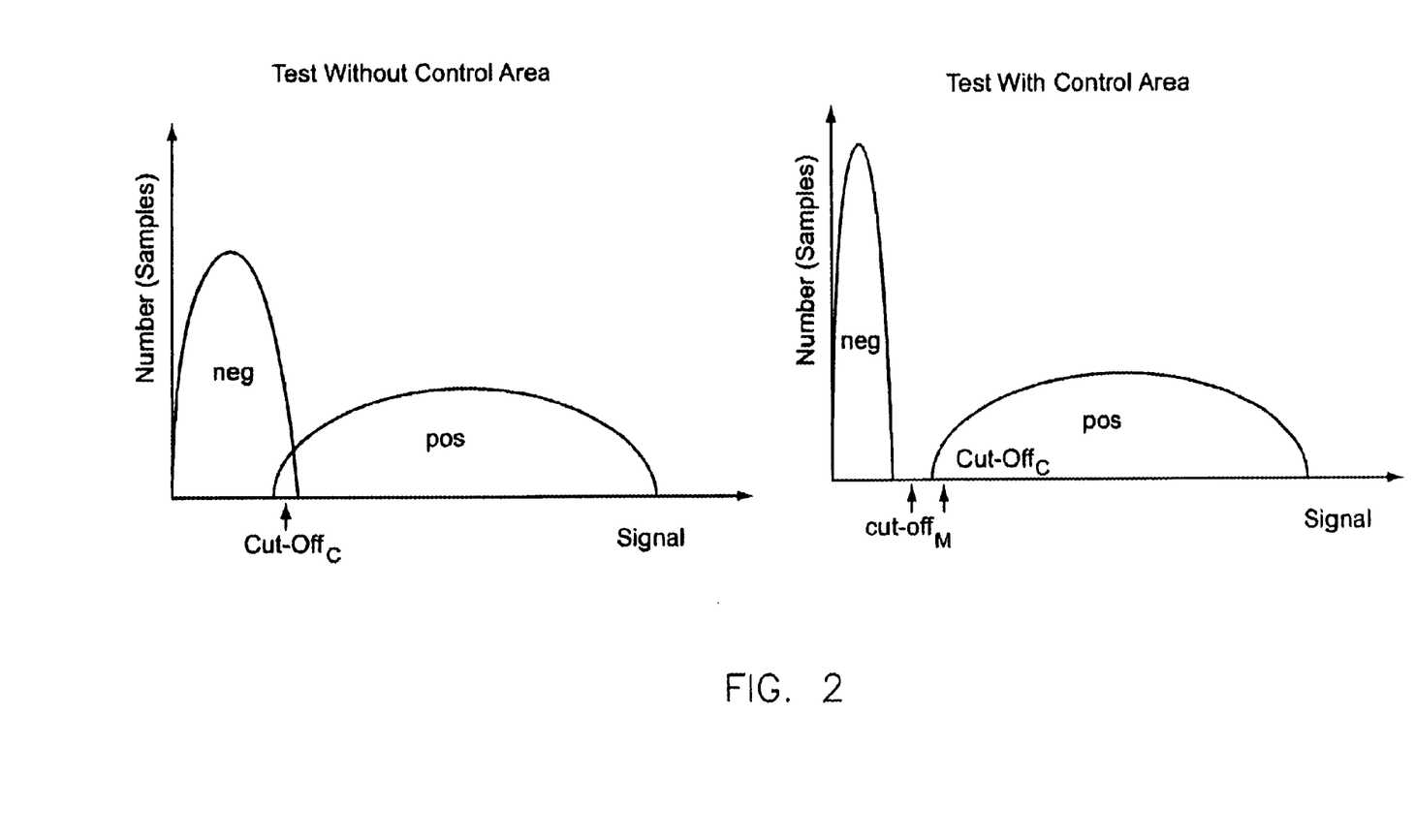
FIG. 2: shows the specificity improvement that is achieved by the use according to the invention of control areas in test formats in which a cut-off value is determined

FIG. 2 shows the effect of a control area used in a test in which a cut-off value is employed. With a large number of samples a certain number of false-negative and false-positive results are obtained (left side) with a conventional test procedure. The use of control areas according to the invention (right side) can selectively reduce the signals from negative samples which leads to a reduction of the cut-off value. In this way a positive/negative differentiation can be made with a considerably reduced probability of error.

A positive control can also be simulated by a reference area which contains the analyte or an analyte-like reagent. A major advantage is that a combination of a negative control area with a positive reference area enables a sample-specific cut-off value to be determined for each individual measurement. An advantage of this is that an indirect calibration is not necessary and an improved test specificity is achieved.

It is of course possible to provide other or/and additional control areas in addition to the aforementioned preferred control areas depending on the test procedure in order to detect interfering components that are presumed to be or are present in a sample.

The control areas provided according to the invention not only enable a qualitative detection of interfering reactions but often also a quantitative correction for the interference. With a suitable selection of test conditions the unspecific binding of non-analyte components occurring in the test areas is accurately reflected in certain control areas. Thus the measured value in a test area can be simply corrected to obtain a correct and unbiased result. Even if the unspecific binding in the test area and the control area are not identical, the measured signal can be corrected in qualitative tests since in this case only a statement of "positive" or "negative" is necessary.

An additional advantage is that the solid phase according to the invention enables the presence of several interfering components to be detected separately and it is possible to determine the type of interference. The user recognizes immediately that the result may be falsified due to the presence of one or several interfering components. The user can then either correct the measured results on the basis of the data that were determined, repeat the measurement with another test format or pretreat the sample in a suitable manner e.g. by separating the interfering components.

The solid phase according to the invention can be used to detect an analyte in a sample e.g. in a body fluid such as blood, serum, plasma, saliva etc. Solid phases with several test areas, i.e. array systems, for the simultaneous detection of several analytes are preferably used. At least one control area is preferably used for each test area in such array systems. The solid phases according to the invention can be used in all known heterogeneous test procedures especially in immunoassays and nucleic acid hybridization assays.

Hence a further subject matter of the invention is a method for the detection of an analyte using a solid phase with at least one defined test area which in addition comprises at least one control area to detect interfering reactions. The method according to the invention preferably includes the use of the control areas for the quantitative correction of interferences.

Finally the invention also concerns the use of control areas in a method for the detection of an analyte for the simultaneous detection of interferences.

The invention is further elucidated by the following figures and examples.

EXAMPLES

Example 1

HBsAg Test Procedure

A monoclonal antibody to HBsAg is applied to a test area of ca. 100 μm on a polystyrene support. A multiple determination can be carried out without additional work when one test is carried out per sample pipetting by applying an identical reagent solution several times. 30 μl sample pre-diluted with sample buffer is pipetted onto the test area and incubated for 20 minutes at room temperature while shaking. After aspirating the sample and washing the test field with wash buffer, 30 μl reagent solution 1 containing digoxigenin(Dig)-labelled anti-HBsAg antibody is added by pipette and again incubated for 20 minutes at room temperature while shaking. After aspirating reagent solution 1 and washing the test field with wash buffer, 30 μl reagent solution 2 containing the detection reagent is pipetted onto the test field. 100 nm fluorescent dyed latex particles which are covalently coated with an anti-Dig antibody are used as a detection reagent. This detection reagent is in turn incubated for 20 minutes at room temperature while shaking, subsequently aspirated, washed and sucked dry. The test field is irradiated with a He—Ne laser at 633 nm wavelength and the fluorescence at 670 nm wavelength is measured with a CCD camera. A schematic representation of this test format is shown in the middle of FIG. 1.

The following test-specific reagents were used:
Solid phase antibody: monoclonal mouse anti-HBsAg antibody 1 (Fab'$_2$ fragment) biotin conjugate 1:1 subtype IgG1
Detection antibody: monoclonal mouse anti-HBsAg antibody 2 IgG-Dig conjugate 1:10

The following test results (counts) were measured:

| Sample | negative control field* (counts) | signal test field (counts) | signal test negative control field | cut-off index** |
|---|---|---|---|---|
| negative control | 22 | 22 | 0 | 0.0 |
| positive contr. 1 (20 U/ml) | 20 | 5459 | 5439 | 82.4 |
| positive contr. 2 (3 U/ml) | 27 | 760 | 733 | 11.1 |
| negative sample 1 | 15 | 15 | 0 | 0.0 |
| negative sample 2 | 15 | 15 | 0 | 0.0 |
| negative sample 3 | 14 | 14 | 0 | 0.0 |
| negative sample 4 | 15 | 15 | 0 | 0.0 |
| negative sample 5 | 15 | 15 | 0 | 0.0 |
| negative sample 6 | 17 | 17 | 0 | 0.0 |

*Negative control field corresponds to the unspecific binding in the control field without solid phase receptor
**Cut-off index: [Signal (test field) − signal (negative control field)]/3 × signal (negative control)

The test is positive at a cut-off>1. The test is negative at a cut-off<1.

Example 2

HBsAg Test With Control Spots to Detect HAMA Interferences

Figure 3:
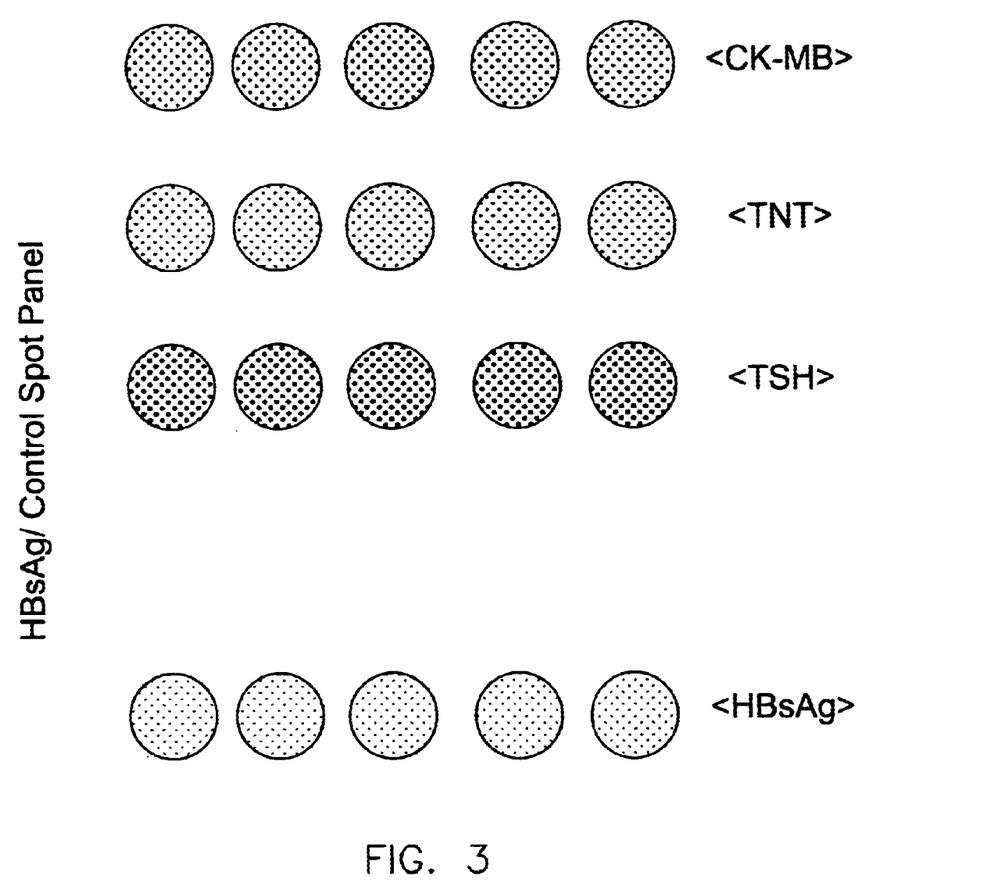
FIG. 3: shows a schematic representation of a solid phase according to the invention for the determination of HBs antigen that contains several control areas (<CK-MB>; <TNT> and <TSH>) in addition to the test area (<HBsAg>).

Additional unspecific monoclonal antibodies (MABs) were applied in addition to HBsAg-specific antibodies to detect HAMA interference (see FIG. 3). Antibodies to creatinine kinase MB (<CK-MB>), Troponin (<TNT>) and thyroid-stimulating hormone (<TSH>) were used in the form of Fab'$_2$ or Fab' biotin conjugates. Due to the fact that the human anti-mouse antibodies in the sample cross-link the unspecific MABs bound to the solid phase and the specific detection antibody it is possible to detect the so-called HAMA interference. The aim of the experiment was to find an optimal MAB for HAMA detection. The HBsAg/control panel was measured with 6 different HAMA samples. For this purpose no or 100 μg/ml HAMA interference-reducing reagent were added to the sample buffer.

a) Experimental Results Without HAMA Interference-reducing Reagent

| Sample | MAB<HBsAg> F(ab')$_2$-Bi 1:1* (counts) | MAB<TSH> F(ab')$_2$-Bi 1:1* (counts) | MAB<TNT> Fab'-Bi 1:1* (counts) | MAB<CK-MB> Fab'-Bi 1:1* (counts) | cut-off index** HBsAg |
|---|---|---|---|---|---|
| neg. contr. | 3 | 18 | 0 | 10 | 0.04 |
| pos. contr. (20 U/ml) | 6169 | 23 | 0 | 5 | 73.4 |
| HAMA 1 | 1598 | 2808 | 741 | 177 | 19.0 |
| HAMA 2 | 4889 | 10434 | 306 | 42 | 58.2 |
| HAMA 3 | 737 | 3728 | 29 | 32 | 8.8 |

-continued

| Sample | MAB<HBsAg> F(ab')$_2$-Bi 1:1* (counts) | MAB<TSH> F(ab')$_2$-Bi 1:1* (counts) | MAB<TNT> Fab'-Bi 1:1* (counts) | MAB<CK-MB> Fab'-Bi 1:1* (counts) | cut-off index** HBsAg |
|---|---|---|---|---|---|
| HAMA 4 | 358 | 2513 | 0 | 0 | 4.3 |
| HAMA 5 | 43 | 2565 | 0 | 0 | 0.5 |
| HAMA 6 | 32157 | 32108 | 32717 | 32930 | 382.8 |

*Signal (test field) − signal (neg. control field)
**Cut-off index = [signal (test field) − signal (negative control field)]/3 × signal (negative control)
signal (negative control) = 28 counts This result shows that 5 of the 6 HAMA samples interfere strongly with the HBsAg test and lead to a false-positive result. The interference can be unambiguously indicated by the presence of the control spots. The TSH-MAB which has an identical cleavage fragment (Fab'$_2$), an identical biotin stoichiometry and identical coupling chemistry is most suitable for this. In contrast the two MABs with Fab' fragments react more poorly than the HBsAg-MAB with the HAMA interfering samples and are therefore less suitable for identifying all HAMA interferences.

b) Experimental Results With 100 μg/ml HAMA Interference-reducing Reagent

| Sample | MAB<HBsAg> F(ab')$_2$-Bi 1:1* (counts) | MAB<TSH> F(ab')$_2$-Bi 1:1* (counts) | MAB<TNT> Fab'-Bi 1:1* (counts) | cut-off index** HBsAg | cut-off index HBsAg$_{corr.}$*** |
|---|---|---|---|---|---|
| neg. contr. | 0 | 0 | 0 | 0.0 | 0.0 |
| pos. contr. (20 U/ml) | 4186 | 0 | 0 | 41.0 | 41.0 |
| HAMA 1 | 0 | 0 | 0 | 0.0 | 0.0 |
| HAMA 2 | 0 | 0 | 0 | 0.0 | 0.0 |
| HAMA 3 | 0 | 0 | 0 | 0.0 | 0.0 |
| HAMA 4 | 0 | 0 | 0 | 0.0 | 0.0 |
| HAMA 5 | 0 | 0 | 0 | 0.0 | 0.0 |
| HAMA 6 | 144 | 187 | 217 | 1.4 | 0.0 |

*Signal (test field) − signal (negative control field)
**cut-off index = (signal (test field) − signal (negative control field)]/3 × signal (negative control)
signal (negative control) = 34 counts
***cut-off index HBsAg$_{corr.}$ = [signal (test field) − signal (MAB control field)]/3 × signal (negative control); definition: negative values = 0

The addition of a very large amount of 100 μg/ml interfering-reducing reagent which would make the test too expensive for routine application enables an interference elimination in 5 of the 6 HAMA samples. However, the HAMA sample 6 remains a problem whose interference cannot be reduced despite the high concentration of interference-reducing reagent. The two control spots can be used to clearly indicate the HAMA interference that is still present. Since the unspecific binding in the TSH control spot corresponds to the unspecific binding in the specific HBsAg spot, the specific signal can be corrected with the aid of the signal in the control spot. With this measure this sample also becomes clearly negative which leads to a considerable improvement of the specificity. Hence the concentration of interference-reducing protein in the sample buffer and thus the production costs can be considerably reduced with the aid of the control spots to improve specificity.

Example 3

HBsAg Test with Control Spots to Detect Sample-specific Matrix Effects

It is generally known that unspecific binding of the detection reagent can be caused by various matrix effects. The application of control spots which have a comparable behaviour towards matrix effects as the test-specific spot enables such matrix effects to be indicated and optionally even to be corrected. This consequently leads to a considerable improvement of specificity.

In the following experiment a HBsAg test was again measured using various HBsAg-negative samples which were selected on the bases of marked matrix effects.

| Sample | MAB<HBsAg> F(ab')$_2$-Bi 1:1* (counts) | MAB<TSH> F(ab')$_2$-Bi 1:1* (counts) | cut-off index** HBsAg | cut-off index HBsAg$_{corr}$*** |
|---|---|---|---|---|
| neg. control | 3 | 18 | 0.04 | 0.0 |
| pos. control (20 U/ml) | 6169 | 23 | 73.4 | 73.2 |
| negative sample 3415 | 0 | 0 | 0.0 | 0.0 |
| negative sample 3418 | 65 | 102 | 0.77 | 0.0 |
| negative sample 4561 | 128 | 494 | 1.52 | 0.0 |
| negative sample 4567 | 158 | 328 | 1.88 | 0.0 |
| negative sample 4609 | 0 | 0 | 0.0 | 0.0 |
| negative sample S21 | 25 | 52 | 0.30 | 0.0 |
| negative sample S25 | 4 | 3 | 0.05 | 0.01 |
| negative sample S45 | 16 | 30 | 0.19 | 0.0 |
| negative sample S49 | 0 | 0 | 0.0 | 0.0 |

*Signal (test field) − signal (negative control field)
**cut-off index = [signal (test field) − signal (negative control field)]/3 × signal (negative control) signal (negative control) = 28 counts
***cut-off index HBsAg$_{corr.}$ = [signal (test field) − signal (MAB control field)]/3 × signal (negative control); definition negative values = 0

Of the measured 9 conspicuously negative samples, 2 samples lead to false-positive results. All samples were brought to zero by correcting the measured value with the aid of a control spot and are thus unequivocally negative.

Example 4

HBsAg Test with Control Areas to Detect Interferences by Rheumatoid Factors

Additional MABs of the IgG1 subtype were applied in addition to the HBsAg-specific antibody in order to detect interference by rheumatoid factors. Since rheumatoid factors can react with the Fc part of antibodies, this can cause a cross-linking of the test-specific MABs bound to the solid phase and the specific detection antibody and thus generate a false-positive reaction. The aim of this experiment was to find the optimal MAB to detect rheumatoid factors. For this reason different MABs of the IgG1 subclass were applied. This HBsAg/control panel was measured with a negative control, 3 different positive controls, 4 normal negative samples and 5 negative samples with increasing amounts of rheumatoid factors (RF 1–5). The respective content of HBsAg in the positive controls and the content of rheumatoid factors in the rheumatoid factor samples is stated in U/ml. The results were as follows:

| Sample | MAB <HBsAG> IgG-Bi [counts] | MAB<IgE> "1"IgG-Bi [counts] | MAB<IgE> "2"IgG-Bi [counts] | MAB<IgE> "3"IgG-Bi [counts] | negative control field* [counts] | cut-off index* HBsAg |
|---|---|---|---|---|---|---|
| neg contr | 27 | 34 | 31 | 30 | 27 | 0.0 |
| pos contr (20 U/ml) | 4701 | 44 | 44 | 44 | 44 | 57.5 |
| pos contr (5 U/ml) | 842 | 43 | 43 | 43 | 43 | 9.9 |
| pos contr (0.1 U/ml) | 106 | 31 | 31 | 31 | 31 | 0.9 |
| neg sample 1 | 30 | 35 | 30 | 30 | 30 | 0.0 |
| neg sample 2 | 28 | 33 | 33 | 34 | 28 | 0.0 |
| neg sample 3 | 29 | 35 | 29 | 29 | 29 | 0.0 |
| neg sample 4 | 27 | 32 | 27 | 27 | 27 | 0.0 |
| RF 1 (307 U/ml) | 39 | 34 | 29 | 30 | 27 | 0.15 |
| RF 2 (421 U/ml) | 41 | 33 | 28 | 28 | 28 | 0.16 |
| RF 3 (1307 U/ml) | 429 | 33 | 115 | 64 | 30 | 4.9 |
| RF 4 (1793 U/ml) | 5790 | 47 | 865 | 204 | 47 | 70.9 |
| RF 5 (2599 U/ml) | 7530 | 106 | 2527 | 759 | 54 | 92.3 |

*cut-off index = (signal (test field) − signal (negative control field)]/3 × signal (negative control)
cut-off index > 1 = positive This example clearly shows that negative samples with a concentration of rheumatoid factors>1000 U/ml considerably interfere with the HBsAg test and lead to a false-positive result. 2 of the 3 tested MAB control areas simulate the interference of the HBsAg test and also yield clearly positive reactions with the 3 high-titre rheumatoid sera. In this manner the test interference is immediately recognized and a false-positive result is avoided. The MAB "2" is most suited to indicate rheumatoid factor interference.

What is claimed is:

1. An assay device for use in the determination of an analyte in a sample, the sample also being suspected of comprising at least one interfering substance, the device comprising:
   a solid phase support;
   a test area for detection of the analyte, the test area comprising test area components in a defined region of the support, the test area components comprising a receptor which includes a binding site for specifically binding with the analyte, and wherein the at least one interfering substance non-specifically binds to one or more test area components; and
   a control area comprising control area components in a separate defined region of the support, wherein the control area components are the same as at least some of the test area components, wherein the at least one interfering substance non-specifically binds to one or more of the control area components and wherein the receptor is absent from or disabled in the control area whereby the analyte does not bind in the control area.

2. The device of claim 1, wherein in the control area the at least one interfering substance binds to substantially the same extent in the control area as in the test area.

3. The device of claim 1, wherein the receptor is absent from the control area.

4. The device of claim 1, wherein a receptor is present in the control area which is identical to the receptor in the test area except that the binding site is absent to thereby prevent specific binding with the analyte in the control area.

5. The device of claim 1, wherein a receptor is present in the control area which is identical to the receptor in the test area except that the binding site is altered to thereby prevent specific binding with the analyte in the control area.

6. The device of claim 1, wherein the control area components are essentially identical to the test area components except that receptor is absent from the control area.

7. The device of claim 1, wherein the control area components are essentially identical to the test area components, including a receptor that is identical to the receptor in the test area except that the binding site is absent on the receptor in the control area to thereby prevent specific binding with the analyte.

8. The device of claim 1, wherein the control area components are essentially identical to the test area components, including a receptor that is identical to the receptor in the test area except that the binding site on the receptor in the control area is altered to thereby prevent specific binding with the analyte.

9. The device of claim 1, wherein the receptor in the test area which includes a binding site for specifically binding with the analyte is selected from the group consisting of antibodies, antibody fragments, antigens, and nucleic acids.

10. The device of claim 1, wherein the interfering substance is selected from serum proteins and serum molecules.

11. The device of claim 1, wherein the interfering substance is selected from the group consisting of rheumatoid factors, foreign-species-specific antibodies, serum components directed against a neo-epitope of an antibody fragment, and antibodies against immobilization reagents on the test area.

12. The device of claim 1, wherein the test area components comprise streptavidin and the interfering substance is a strepavidin-binding component.

13. The device of claim 1, further comprising a positive reference area comprising the analyte.

14. The device of claim 1, wherein the test area and the control area each have a diameter of 10 μm to 1 cm.

15. The device of claim 1, wherein the test area is present in the form of multiple defined test areas, each of the test areas spatially separated from each other by an inert region and comprising test area components in a defined region of the support, the test area components comprising a receptor which includes a binding site for specifically binding with the analyte.

16. The device of claim 15, further comprising a plurality of corresponding control areas.

17. The device of claim 1, further comprising a second test area comprising second test area components in a separate defined region of the support, the second test area components comprising a second receptor which includes a binding site for specifically binding with a second analyte, and wherein the at least one interfering substance is capable of non-specific binding to one or more of the second test area components.

18. The device of claim 1, wherein the analyte is selected from the group consisting of HIV antibodies, HBs antigens, and HBc antibodies.

19. An assay method for determining an analyte in a sample, the sample also suspected of comprising at least one interfering substance, the method comprising:
  a. applying the sample to a solid phase support, the support including:
    i. a test area for detection of the analyte, the test area comprising test area components in a defined region of the support, the test area components comprising a receptor which includes a binding site for specifically binding with the analyte, and wherein the at least one interfering substance non-specifically binds to one or more test area components, and
    ii. a control area comprising control area components in a separate defined region of the support, wherein the control area components are the same as at least some of the test area components, wherein the at least one interfering substance non-specifically binds to one or more of the control area components and wherein the receptor is absent from or disabled in the control area whereby the analyte does not bind in the control area;
  b. applying a marker to the solid phase support to generate a detectable signal;
  c. measuring the signal generated by the marker in the test area; and
  d. measuring the signal generated by the marker in the control area.

20. The assay method of claim 19, further comprising quantitatively determining the amount of the analyte in the sample by correcting the value determined in step (c) of claim 19, with the value determined in step (d) of claim 19.

21. The assay method of claim 19, wherein in the control area the at least one interfering substance binds to substantially the same extent in the control area as in the test area.

22. The assay method of claim 19, wherein the quantitative determination comprises subtracting the value determined in (d) of claim 19, from the value determined in step (c) of claim 19.

23. The assay method of claim 19, wherein the receptor is absent from the control area.

24. The assay method of claim 19, wherein a receptor is present in the control area which is identical to the receptor in the test area except that the binding site is absent to thereby prevent specific binding with the analyte in the control area.

25. The assay method of claim 19, wherein a receptor is present in the control area which is identical to the receptor in the test area except that the binding site is altered to thereby prevent specific binding with the analyte in the control area.

26. The assay method of claim 19, wherein the control area components are essentially identical to the test area components except receptor is absent from the control area.

27. The assay method of claim 19, wherein the control area components are essentially identical to the test area components, including a receptor that is identical to the receptor in the test area except that the binding site is absent on the receptor in the control area to thereby prevent specific binding with the analyte.

28. The assay method of claim 19, wherein the control area components are essentially identical to the test area components, including a receptor that is identical to the receptor in the test area except that the binding site is altered on the receptor in the control area to thereby prevent specific binding with the analyte.

29. The assay method of claim 19, wherein the receptor which includes a binding site for specifically binding with the analyte is selected form the group consisting of antibodies, antibody fragments, antigens, and nucleic acids.

30. The assay method of claim 19, wherein the analyte is selected from the group consisting of HIV antibodies, HBs antigens, HBc antibodies, and nucleic acids.

31. The assay method of claim 19, wherein the interfering substance is selected from the group consisting of rheumatoid factors, foreign-species-specific antibodies, serum components directed against a neo-epitope of an antibody fragment, and antibodies against immobilization reagents on the test area.

32. The assay method of claim 19, wherein the assay is an immunoassay and the binding component for the analyte is selected from the group consisting of antibodies, antigens, and fragments thereof.

33. The assay method of claim 19, wherein the assay is a nucleic acid hybridization assay and the binding component for the analyte is a nucleic acid segment.

34. A kit for use in the determination of an analyte in a sample, the sample also being suspected of comprising at least one interfering substance, the kit comprising:
  a. a solid phase support including:
    i. a test area for detection of the analyte, the test area comprising test area components in a defined region of the support, the test area components comprising a receptor which includes a binding site for specifically binding with the analyte, and wherein the at least one interfering substance non-specifically binds to one or more test area components,
    ii. a control area comprising control area components in a separate defined region of the support, wherein the control area components are the same as at least some of the test area components, wherein the at least one interfering substance non-specifically binds to one or more of the control area components and wherein the receptor is absent from or disabled in the control area whereby the analyte does not bind in the control area; and
  b. a marker capable of binding to the analyte and to the at least one interfering substance, the marker adapted to allow quantitative determination of the analyte and at least one interfering substance.

\* \* \* \* \*